US011304925B1

(12) United States Patent
Karelis et al.

(10) Patent No.: US 11,304,925 B1
(45) Date of Patent: Apr. 19, 2022

(54) CANNABIS COMPOSITION

(71) Applicant: ZELDA THERAPEUTICS OPERATIONS PTY LTD, Perth (AU)

(72) Inventors: Harry Karelis, Perth (AU); Mara Gordon, Bodega Bay, CA (US); Stewart Smith, Bodega Bay, CA (US); Stewart Washer, Stirling (AU)

(73) Assignee: ZELDA THERAPEUTICS OPERATIONS PTY LTD, Perth (AU)

( * ) Notice: Subject to any disclaimer, the term of this patent is extended or adjusted under 35 U.S.C. 154(b) by 121 days.

(21) Appl. No.: 15/780,579

(22) PCT Filed: Aug. 3, 2017

(86) PCT No.: PCT/AU2017/050817
§ 371 (c)(1),
(2) Date: May 31, 2018

(87) PCT Pub. No.: WO2018/023166
PCT Pub. Date: Feb. 8, 2018

Related U.S. Application Data

(60) Provisional application No. 62/370,299, filed on Aug. 3, 2016.

(30) Foreign Application Priority Data

Apr. 4, 2017 (AU) .............................. 2017901222
May 31, 2017 (AU) .............................. 2017902065

(51) Int. Cl.
| | | |
|---|---|---|
| *A61K 31/352* | (2006.01) | |
| *A61P 35/00* | (2006.01) | |
| *A61K 31/05* | (2006.01) | |
| *A61K 45/06* | (2006.01) | |

(52) U.S. Cl.
CPC ............ *A61K 31/352* (2013.01); *A61K 31/05* (2013.01); *A61K 45/06* (2013.01); *A61P 35/00* (2018.01)

(58) Field of Classification Search
CPC ...... A61K 31/352; A61K 31/05; A61K 45/06; A61P 35/00
USPC ........................................................ 514/454
See application file for complete search history.

(56) References Cited

U.S. PATENT DOCUMENTS

| | | | |
|---|---|---|---|
| 8,895,078 B2 | 11/2014 | Mueller | |
| 9,044,390 B1 | 6/2015 | Speier | |
| 2007/0060639 A1 | 3/2007 | Wemeling | |
| 2012/0263785 A1 | 10/2012 | Rossi et al. | |
| 2014/0271940 A1 | 9/2014 | Wurzer | |
| 2014/0314757 A1 | 10/2014 | Sanchez et al. | |
| 2016/0106705 A1 | 4/2016 | Verzura et al. | |
| 2016/0346339 A1* | 12/2016 | Finley .................. | A61K 31/355 |

FOREIGN PATENT DOCUMENTS

| | | |
|---|---|---|
| EP | 1802274 A1 | 7/2007 |
| JP | 2008/523078 A | 7/2008 |
| JP | 2014/530247 A | 11/2014 |
| WO | 2011/110866 A1 | 9/2011 |
| WO | WO-2013/057487 | 4/2013 |
| WO | 2013/165251 A1 | 11/2013 |
| WO | 2014/145490 A2 | 9/2014 |
| WO | 2015/065544 A1 | 5/2015 |
| WO | 2015/200049 A1 | 12/2015 |
| WO | 2016/030369 A1 | 3/2016 |
| WO | WO-2016/064987 | 4/2016 |
| WO | WO-2016/094810 | 6/2016 |
| WO | 2016/123475 A1 | 8/2016 |
| WO | WO-2018/023163 | 2/2018 |
| WO | WO-2018/023164 | 2/2018 |

OTHER PUBLICATIONS

Chakravarti B., et al., "Cannabinoids as therapeutic agents in cancer: current status and future implications," Oncotarget, vol. 5, No. 15, pp. 5852-5872.
McAllister, S.D., et al., "Cannabidiol as a novel inhibitor of Id-1 gene expression in aggressive breast cancer cells," Molecular Cancer Therapeutics 2007; 6(1) Nov. 2007, pp. 2921-2927.
International Search Report dated Nov. 20, 2017 for PCT Application No. PCT/AU2017/050817 filed Aug. 3, 2017, 7 pages.
Written Opinion dated Nov. 20, 2017 for PCT Application No. PCT/AU2017/050817 filed Aug. 3, 2017, 4 pages.
Hazekamp and Fischedick, "Cannabis—from cultivator to chemovar," Drug Testing Analysis, 4(7-8), pp. 660-667 (2012).
Chang and Shen, "Linalool Exhibits Cytotoxic Effect by Activating Antitumor Immunity," Molecules, 19, pp. 6694-6706 (2014).
Caffarel et al., "Cannabinoids: A new hope for breast cancer therapy?" Cancer Treatment Reviews, 38, pp. 911-918 (2012).
Russo, "Taming THC: potential cannabis synergy and phytocannabinoid-terpenoid entourage effects," British Journal of Pharmacology, 163, pp. 1344-1364 (2011).
Sharma et al., "Polypharmacological Properties and Therapeutic Potential of β-Caryophyllene: A Dietary Phytocannabinoid of Pharmaceutical Promise," Current Pharmaceutical Design, 22(21), pp. 3237-3264 (2016); Abstract only.
Guindon and Hohmann, "The endocannabinoid system and cancer: therapeutic implication," Br. J. Pharmacol., 163(7), pp. 1447-143 (2011).
Murase et al., "Targeting multiple cannabinoid anti-tumor pathways with a resorcinol derivative leads to inhibition of advanced stages of breast cancer," Br. J. Pharmacol., 171(19), pp. 4464-4477 (2014).
Columbian Office Action dated Jun. 28, 2021 issued against corresponding CO Patent Application No. NC2019/0001043 together with an English translation.

\* cited by examiner

*Primary Examiner* — Yevgeny Valenrod
(74) *Attorney, Agent, or Firm* — Mintz, Levin, Cohn, Ferris, Glovsky and Popeo, P.C.

(57) ABSTRACT

The invention relates to a method for treating cancer or a symptom associated with cancer. In particular, the present invention relates to a method for treating cancer or a symptom associated with cancer, comprising administering to a patient in need thereof an effective amount of the pharmaceutical composition comprising a *Cannabis* extract that comprises $\Delta^9$-tetrahydrocannabinol (THC) in an amount of from 50% to 99% by weight of the pharmaceutical composition.

9 Claims, 5 Drawing Sheets

A

B

C

A

B

A

B

CANNABIS COMPOSITION

FIELD

The invention relates to a method for treating cancer or a symptom associated with cancer. The invention also relates to a pharmaceutical composition comprising an extract from a *Cannabis* plant, and its use in the treatment of cancer or a symptom associated with cancer.

BACKGROUND

The biological activity of *Cannabis* is well known, and has led it to become a "recreational" drug. However, with the discovery of a class of cannabinoid (CB) receptors, and the relaxation of laws regulating *Cannabis* use—in some jurisdictions decriminalisation—there now exists the opportunity to explore the potential of *Cannabis* as a source of new therapeutics.

There is also a growing movement of patients suffering from severe diseases, such as cancer, to seek natural remedies as alternative or complementary therapy.

Accordingly, there is a continuing need to develop new treatments for cancer or its symptoms, which is derived, at least in part, from a natural source. Advantageously, the present invention may provide a pharmaceutical composition comprising a *Cannabis* extract that shows an efficacy comparable to an existing cancer chemotherapy.

SUMMARY

The invention provides a method of treating cancer or a symptom associated with cancer comprising administering to a patient in need thereof an effective amount of a pharmaceutical composition comprising a *Cannabis* extract. Accordingly, also provided is a pharmaceutical composition comprising a *Cannabis* extract and optionally one or more pharmaceutically acceptable carriers, diluents, adjuvants, excipients or any combination thereof.

In a further aspect, there is provided use of a *Cannabis* extract in the preparation of a medicament for treating cancer or a symptom associated with cancer.

In yet another aspect, there is provided a pharmaceutical composition for treating cancer or a symptom associated with cancer, wherein the pharmaceutical composition comprises a *Cannabis* extract and optionally one or more pharmaceutically acceptable carriers, diluents, adjuvants, excipients or any combination thereof.

BRIEF DESCRIPTION OF DRAWINGS

The present application will be further described, by way of example only, with reference to the accompanying drawings, in which.

DESCRIPTION OF EMBODIMENT(S)

Figure 1:
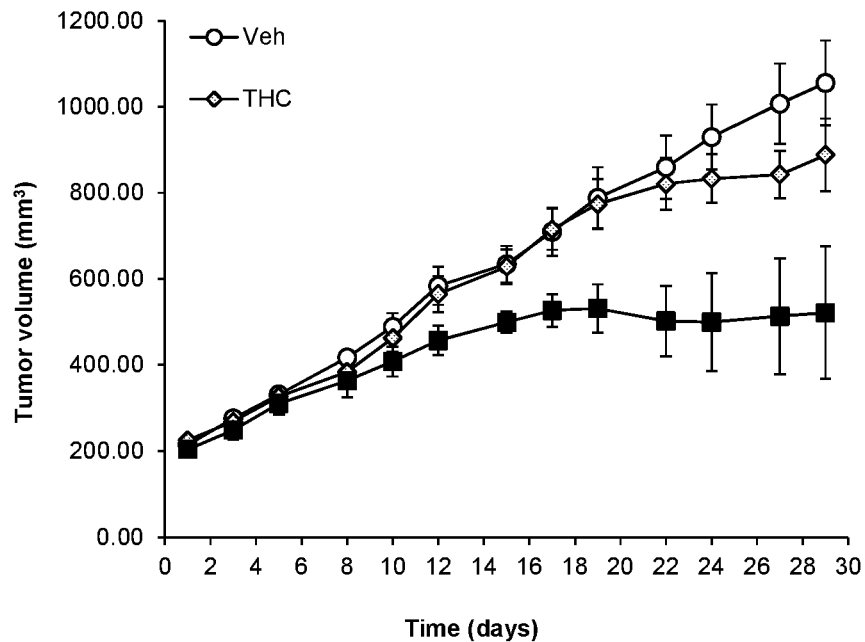
FIG. 1 shows a chart of tumour volume over time for ectopic xenografts of BT474 human breast HER2+ adenocarcinoma cells in female immunodeficient (nude) mice treated with (i) vehicle alone, (ii) THC and (iii) a *Cannabis* extract.

The present invention provides a pharmaceutical composition comprising a *Cannabis* extract and optionally one or more pharmaceutically acceptable carriers, diluents, adjuvants, excipients or any combination thereof.

*Cannabis* plants produce a diverse array of secondary metabolites, including cannabinoids, terpenes and terpenoids, sterols, triglycerides, alkanes, squalenes, tocopherols, carotenoids and alkaloids. The mix of these secondary metabolites varies depending on several factors, including *Cannabis* variety, part of the *Cannabis* plant extracted, method of extraction, processing of the extract, and season.

There are several varieties of *Cannabis* plant, which have been described under two distinct naming conventions. One of these conventions identifies three distinct species of *Cannabis* plant, namely *Cannabis sativa* Linnaeus, *Cannabis indica* LAM., and *Cannabis ruderalis*. Another convention identifies all *Cannabis* plants as belonging to the *Cannabis sativa* L. species, with the various varieties divided amongst several subspecies, including: *Cannabis sativa* ssp. *sativa* and ssp. *indica*. As used herein, the term "*Cannabis*" refers to any and all of these plant varieties.

Extracts of *Cannabis* may be prepared by any means known in the art. The extracts may be formed from any part of the *Cannabis* plant containing cannabinoid, terpene and terpenoid compounds. Extracts may be formed by contacting an extractant with a leaf, seed, trichome, flower, keif, shake, bud, stem or a combination thereof. In some embodiments, the extract is formed from the flowers and shake of a *Cannabis* plant. Any suitable extractant known in the art may be used, including, for example, alcohols (e.g. methanol, ethanol, propanol, butanol, propylene glycol etc.), water, hydrocarbons (e.g. butane, hexane, etc.), oils (e.g. olive oil, vegetable oil, essential oil, etc.), a polar organic solvent (e.g. ethyl acetate, polyethylene glycol, etc.) or a supercritical fluid (e.g. liquid $CO_2$). The extractant may be completely or partially removed prior to incorporation of the *Cannabis* extract into the pharmaceutical composition, or it may be included in the pharmaceutical composition as a carrier. The extractant may be removed by heating the extract optionally under reduced pressure (e.g. under vacuum). It will be appreciated that some of the more volatile plant metabolites (such as terpenes) may also be removed with the extractant. Accordingly, in some embodiments, removing the extractant may enrich the cannabinoid fraction of the extract. In some embodiments, the extract is filtered to remove particulate material, for example, by passing the extract through filter paper or a fine sieve (e.g. a sieve with pore sizes of 5 µm).

In some embodiments, the *Cannabis* extract is formed by applying heat and pressure to the plant material. Typically, in these embodiments, no extractant is required.

In some embodiments, the *Cannabis* extract is a *Cannabis* oil. As used herein, a "*Cannabis* oil" is an extract formed by contacting at least a part of a *Cannabis* plant with an oil. The extracting oil may optionally be removed. Extracting oils may be selected from olive oil, hemp oil, sesame oil, coconut oil, vegetable oil, canola oil, grape seed oil, almond oil, medium-chain triglyceride (MCT) oil, and any other edible oil, or a combination thereof.

In some embodiments, one or more additional compounds (e.g. cannabinoid, terpene or terpenoid compounds) may be added to the *Cannabis* extract. The addition of compounds may be to compensate for natural variations in the relative amounts of certain compounds being expressed in the *Cannabis* plant. The added compounds may be synthetic versions of the desired compounds, they may be purified compounds obtained from other *Cannabis* extracts, or they may be added by blending two or more *Cannabis* extracts.

The term "cannabinoid" as used herein relates to any cannabinoid that have been isolated from a *Cannabis* plant or synthetically created to have activity involving the endocannabinoid system.

The term "cannabinoid fraction" is used to describe the combination of cannabinoid compounds present in the *Cannabis* extract.

The term "terpenes" or "terpenoids" as used herein refers to a class of hydrocarbon molecules, which often provide a unique smell. Terpenes are derived from units of isoprene, which has the molecular formula $C_5H_8$. The basic molecular formula of terpenes are multiples of the isoprene unit, i.e. $(C_5H_8)_n$, where n is the number of linked isoprene units. Terpenoids are terpene compounds that have been further metabolised in the plant, typically through an oxidative process, and therefore usually contain at least one oxygen atom.

The term "terpene fraction" is used to describe the combination of terpene and terpenoid compounds present in the *Cannabis* extract.

One embodiment provides a pharmaceutical composition comprising a *Cannabis* extract and optionally one or more pharmaceutically acceptable carriers, diluents, adjuvants, excipients or any combination thereof, wherein the *Cannabis* extract comprises either:

A.
  ≥0.3% w/w of the terpene fraction;
  ≥50% w/w $\Delta^9$-Tetrahydrocannabinol (THC);
  ≥0.3% w/w Cannabigerol (CBG); and
  ≤0.5% w/w Cannabinol (CBN)
or
B.
  ≥0.5% w/w of the terpene fraction;
  ≥60% w/w CBD;
  ≤3% w/w THC; and
  ≤0.1% w/w CBN.

Another embodiment provides a pharmaceutical composition comprising a *Cannabis* extract and optionally one or more pharmaceutically acceptable carriers, diluents, adjuvants, excipients or any combination thereof, the *Cannabis* extract comprising a terpene fraction comprising:
  ß-caryophyllene in an amount of at least 11% by weight of the terpene fraction, and
  one or more of:
  linalool in an amount of at least 5% by weight of the terpene fraction; and
  ß-pinene in an amount of at least 1% by weight of the terpene fraction.

Cannabinoid Fraction

The cannabinoid fraction typically accounts for the majority of the compounds present in the *Cannabis* extract.

In some embodiments, the *Cannabis* extract may comprise about 35% to about 95% by weight cannabinoids, for example, about 40% to about 90%, about 45% to about 70% or about 45% to about 55% by weight of the *Cannabis* extract. In some embodiments, the *Cannabis* extract comprises about 5% to about 65% by weight of non-cannabinoids, for example, about 5% to about 50%, about 10% to about 40% by weight or about 15% to about 30% by weight non-cannabinoids.

To date, over 100 cannabinoids have been identified in *Cannabis* plants. A comprehensive list of these cannabinoids may be found in Mahmoud A. El Sohly and Waseem Gul, "Constituents of *Cannabis Sativa*." In *Handbook of Cannabis* Roger Pertwee (Ed.) Oxford University Press (2014) (ISBN: 9780199662685). Cannabinoids that have been identified in *Cannabis* plants include: Cannabigerol (E)-CBG-C5, Cannabigerol monomethyl ether (E)-CBGM-C5 A, Cannabigerolic acid A (Z)-CBGA-C5 A, Cannabigerovarin (E)-CBGV-C3, Cannabigerolic acid A (E)-CBGA-C5 A, Cannabigerolic acid A monomethyl ether (E)CBGAM-C5 A and Cannabigerovarinic acid A (E)-CBGVAC3A; (±)-Cannabichromene CBC-C5, (±)-Cannabichromenic acid A CBCA-C5 A, (±)-Cannabivarichromene, (±)-Cannabichromevarin CBCV-C3, (±)-Cannabichromevarinic acid A CBCVA-C3 A; (−)-Cannabidiol CBD-C5, Cannabidiol momomethyl ether CBDMC5, Cannabidiol-C4 CBD-C4, (−)-Cannabidivarin CBDVC3, Cannabidiorcol CBD-CI, Cannabidiolic acid CBDA-C5, Cannabidivarinic acid CBDVA-C3; Cannabinodiol CBNDC5, Cannabinodivarin CBND-C3; $\Delta^9$-Tetrahydrocannabinol $\Delta^9$-THC-C5, $\Delta^9$-Tetrahydrocannabinol-C4 $\Delta^9$-THCC4, $\Delta^9$-Tetrahydrocannabivarin $\Delta^9$-THCV-C3, $\Delta^9$-Tetrahydrocannabiorcol $\Delta^9$-THCO-CI, $\Delta^9$-Tetrahydrocannabinolic acid A $\Delta^9$-THCA-C5 A, $\Delta^9$-Tetrahydrocannabinolic acid B $\Delta^9$-THCA-C5 B, $\Delta^9$-Tetrahydrocannabinolic acid-C4 A and/or B $\Delta^9$-THCA-C4 A and/or B, $\Delta^9$-Tetrahydro-cannabivarinic acid A $\Delta^9$-THCVA-C3 A, $\Delta^9$-Tetrahydrocannabiorcolic acid A and/or B $\Delta^9$-TH-COA-CI A and/or B), (−)-$\Delta^8$-trans-(6aR,10aR)-$\Delta^8$-Tetrahydrocannabinol $\Delta^8$-THC-C5, (−)-$\Delta^8$-trans-(6aR,10aR)-Tetrahydrocannabinolic acid A $\Delta^8$-THCA-C5 A, (−)-(6aS,10aR)-$\Delta^9$-Tetrahydrocannabinol (−)-cis-$\Delta^9$-THC-C5; Cannabinol CBN-C5, Cannabinol-C4 CBN-C4, Cannabivarin CBN-C3, Cannabinol C2 CBN-C2, Cannabiorcol CBN-CI, Cannabinolic acid A CBNA-C5 A, Cannabinol methyl ether CBNM-C5, (−)-(9R,10R)-trans-Cannabitriol (−)-trans-CBT-C5, (+)-(9S,10S)-Cannabitriol (+)-trans-CBT-C5, (±)-(9R,10S/9S,10R)—); Cannabitriol (±)-cis-CBT-C5, (−)-(9R,10R)-trans-10-O-Ethyl-cannabitriol (−)-trans-CBT-OEt-C5, (±)-(9R,10R/9S,10S)-Cannabitriol-C3 (±)-trans-CBT-C3, 8,9-Dihydroxy-$\Delta$6a(10a)-tetrahydrocannabinol 8,9-Di-OH-CBT-C5, Cannabidiolic acid A cannabitriol ester CBDA-C5 9-OH-CBT-C5 ester, (−)-(6aR,9S,10S, 10aR)-9,10-Dihydroxyhexahydrocannabinol, Cannabiripsol, Cannabiripsol-C5, (−)-6a,7,10a-Trihydroxy-$\Delta^9$-tetrahydrocannabinol (−)-Cannabitetrol, 10-Oxo-$\Delta$6a (10a)tetrahydrocannabinol OTHC); (5aS,6S,9R,9aR)-Cannabielsoin CBE-C5, (5aS,6S,9R,9aR)-C3-Cannabielsoin CBE-C3, (5aS,6S,9R,9aR)-Cannabielsoic acid A CBEA-C5 A, (5aS,6S,9R,9aR)-Cannabielsoic acid B CBEA-C5 B; (5aS,6S,9R,9aR)-C3-Cannabielsoic acid B CBEA-C3 B, Cannabiglendol-C3 OH-iso-HHCV-C3, Dehydrocannabifuran DCBF-C5, Cannabifuran CBF-C5), (−)-$\Delta^7$-trans-(1R, 3R,6R)-Isotetrahydrocannabinol, (±)-$\Delta^7$-1,2-cis-(1R,3R,6S/ 1S,3S,6R)-Isotetrahydrocannabivarin, (−)-$\Delta^7$-trans-(1R,3R, 6R)-Isotetrahydrocannabivarin; (±)-(laS,3aR,8bR,8cR)-Cannabicyclol CBL-C5, (±)-(1aS,3aR,8bR,8cR)-Cannabicyclolic acid A CBLA-C5 A, (±)-(laS,3aR,8bR, 8cR)-Cannabicyclovarin CBLV-C3; Cannabicitran CBTC5; Cannabichromanone CBCN-C5, Cannabichromanone C3 CBCN-C3, and Cannabicoumaronone CBCON-C5.

The cannabinoid fraction may comprise a main cannabinoid. $\Delta^9$-Tetrahydrocannabinol (THC) or cannabidiol (CBD) may be the main cannabinoid. The main cannabinoid may be present in the *Cannabis* extract in an amount of at least about 40%, about 45%, about 50% or about 55% by weight of the *Cannabis* extract. Accordingly, when THC is the main cannabinoid, the *Cannabis* extract may comprise at least about 40%, 45%, 50% or 55% by weight $\Delta^9$-tetrahydrocannabinol (THC), for example, 40-97% or 50-90% by weight of $\Delta^9$-tetrahydrocannabinol (THC). When CBD is the main cannabinoid, the *Cannabis* extract may comprise at least about 40%, 45%, 50%, 55% or 60% by weight CBD, for example, 40-97% or 50-90% by weight of CBD.

In some embodiments, the *Cannabis* extract is enriched in one or the other of THC or CBD. It has been shown that endocannabinoids (i.e. naturally occurring cannabinoids), including THC and CBD, interact with a class of G protein-coupled receptors (GPCRs) named the "cannabinoid receptors", e.g. the CB1 or CB2 receptors. However, structurally related cannabinoid compounds may have vastly different activity. For example, it has been reported that THC is a CB1 agonist, and that CBD is a CB1 antagonist. Accordingly, in the present invention, the *Cannabis* extract contains 50-90% by weight of only one of THC and CBD. It will be appreciated that *Cannabis* extracts comprising 50-90% of THC, may comprise low amounts of CBD, for example, less than 50% by weight CBD, or less than 40%, 30%, 20%, 15%, 10%, 5%, 4%, 3%, 2%, 1%, 0.5% or 0.1% by weight CBD, or may not comprise any measurable amount of CBD. Similarly, *Cannabis* extracts comprising 50-90% of CBD, may comprise low amounts of THC, for example, less than 50% by weight THC, or less than 40%, 30%, 20%, 15%, 10%, 5%, 4%, 3%, 2%, 1%, 0.5% or 0.1% by weight THC or may not comprise any measurable amount of THC.

In some embodiments, the *Cannabis* extract may comprise 50-80% by weight THC or CBD, 50-75% by weight THC or CBD, 50-70% by weight THC or CBD, 50-65% by weight THC or CBD, 52-80% by weight THC or CBD, 53-80% THC or CBD, or 52-65% by weight THC or CBD.

In some embodiments, the *Cannabis* extract may comprise THC and CBD in a combined weight of 50-90% by weight of the composition. In these embodiments, the ratio of THC to CBD may be about 1:1, for example, the ratio of THC to CBD may be from 100:0 to 0:100, 100:1 to 1:100, 80:1 to 1:80, 60:1 to 1:60, 40:1 to 1:40 or 20:1 to 1:20.

Typically, the *Cannabis* extract may also comprise other cannabinoids in addition to THC and/or CBD. These cannabinoids include—Tetrahydrocannabinolic acid (THCA), $\Delta^9$-Tetrahydrocannabivarin (THCV), (−)-Cannabidivarin (CBDV), Cannabinol (CBN) and Cannabigerol (CBG). Each of these cannabinoids may be present in an amount from 0.001% to 40% by weight of the *Cannabis* extract. For example, CBN may be present in an amount of not more than 0.5% by weight of the extract, for example, not more than 0.4%, 0.3%, 0.2% or 0.1% by weight of the extract. CBN may be present in the *Cannabis* extract in an amount of 0.001-0.5% or 0.001-0.1% by weight. CBG may be present in an amount of at least 0.3% by weight of the extract, for example, 0.3-10% or 0.35-5% by weight of the extract.

In some embodiments, certain cannabinoids may be absent, or present in non-detectable amounts (e.g. less than 0.001% by weight of the analyte). In some embodiments, the *Cannabis* extract may exclude one or more of the following cannabinoids: $\Delta^9$-Tetrahydrocannabivarin (THCV), Cannabidiolic acid (CBDA), Cannabinol (CBN), (−)-Cannabidivarin (CBDV) and Cannabichromene (CBC).

Terpene Fraction

The *Cannabis* extract comprises non-cannabinoid compounds, which typically includes a terpene fraction. In some embodiments, the *Cannabis* extract comprises a terpene fraction in an amount of less than 50% by weight, for example, less than 45%, 40%, 35%, 30%, 25%, 20%, 15%, 10%, 9%, 8%, 7%, 6%, 5%, 4%, 3%, 2% or 1% by weight of the extract. In some embodiments, the *Cannabis* extract may comprise terpene and terpenoid compounds in an amount of at least 0.001% by weight of the extract, for example, at least 0.005%, 0.01%, 0.05%, 0.1%, 0.2%, 0.25%, 0.3%, 0.35%, 0.4%, 0.45%, 0.5%, 1%, 2%, 3%, 4%, 5%, 6%, 10%, 15% or more of the total weight of the extract. In some embodiments, the *Cannabis* extract comprises about 0.001% to about 50% by weight of terpene and terpenoid compounds, for example, about 0.01% to about 50% by weight, about 0.01% to about 10% by weight, about 0.01% to about 6% by weight or about 0.01 to about 5% by weight of the composition.

Typically, the terpene fraction in the plant material used to form the extract may have a different terpene/terpenoid profile than the terpene profile of the final extract, both in terms of the amounts of specific compounds in the terpene fraction and the weight of the terpene fraction relative to the other components. For example, a *Cannabis* flower may comprise about 20% by weight cannabinoids and about 3% by weight terpenes. Following extraction and concentration (i.e. removal of the extractant), the amount of cannabinoids may increase to an amount of about 50-90% by weight and the terpene fraction may amount to about 0.1-6% by weight of the *Cannabis* extract. This typical scenario shows that while the cannabinoids are concentrated when the extractant is removed, the relative amount of the terpene fraction is reduced, likely due to the volatility of many of the terpenes/ terpenoids present in the terpene fraction. Therefore, the profile of the terpene fraction present in the *Cannabis* extract is significantly different from the profile of the terpene fraction that exists in Nature.

The efficacy of a pharmaceutical composition may be enhanced when the terpene fraction has a certain profile, i.e. a certain proportion of particular terpenes/terpenoids are present in the extract. It is believed that the increase in efficacy may be synergistic (i.e. non-additive). It is also believed that the presence of specific components in the terpene fraction may enhance the patient's tolerance to cannabinoid therapy.

A variety of terpenes and terpenoids have also been identified in *Cannabis* extracts, including monoterpenes, monoterpenoids, sesquiterpenes and sesquiterpenoids. For example, the following terpenes and terpenoids have been identified in *Cannabis* extracts: Alloaromadendrene, allyl hexanoate, benzaldehyde, (Z)-a-cis-bergamotene, (Z)-a- trans-bergamotene, ß-bisabolol, epi-a-bisabolol, ß-bisabolene, borneol (camphol), cis-y-bisabolene, borneol acetate (bornyl acetate), α-cadinene, camphene, camphor, cis-carveol, caryophyllene (ß-caryophyllene), α-humulene (α-caryophyllene), γ-cadinene, Δ-3-carene, caryophyllene oxide, 1,8-cineole, citral A, citral B, cinnameldehyde, α-copaene (aglaiene), γ-curcumene, ß-cymene, ß-elemene, γ-elemene, ethyl decadienoate, ethyl maltol, ethyl propionate, ethylvanillin, eucalyptol, α-eudesmol, ß-eudesmol, γ-eudesmol, eugenol, cis-ß-farnesene ((Z)-ß-farnesene), trans-α-farnesene, trans-ß-farnesene, trans-γ-bisabolene, fenchone, fenchol (norbornanol, ß-fenchol), geraniol, α-guaiene, guaiol, methyl anthranilate, methyl salicylate, 2-methyl-4-heptanone, 3-methyl-4-heptanone, hexyl acetate, ipsdienol, isoamyl acetate, lemenol, limonene, d-limonene (limonene), linolool (linalyl alcohol, ß-linolool), α-longipinene, menthol, γ-muurolene, myrcene (ß-myrcene), nerolidol, trans-nerolidol, nerol, ß-ocimene (cis-ocimene), octyl acetate, α-phellandrene, phytol, α-pinene (2-pinene), ß-pinene, pulegone, sabinene, cis-sabinene hydrate (cis-thujanol), ß-selinene, α-selinene, γ-terpinene, terpinolene (isoterpine), terpineol (α-terpineol), terpineol-4-ol, α-terpinene (terpilene), α-thujene (origanene), vanillin, viridiflorene (ledene), and α-ylange.

It is believed that the presence of the particular terpenes/terpenoids in the specified amounts present in the terpene fraction is associated with increased efficacy of the pharmaceutical composition in in vivo studies (see Example 2).

The *Cannabis* extract included in the pharmaceutical compositions comprises ß-caryophyllene in an amount of at least 11% by weight of the terpene fraction. It is believed that ß-caryophyllene may counteract the sedative effects of some of the cannabinoids.

In some embodiments, the extract comprises ß-caryophyllene in amount of at least about 11%, about 12%, about 13%, about 14% or about 15% by weight of the terpene fraction. In some embodiments, the extract comprises less than about 60%, about 55%, about 50%, or about 45% by weight of the terpene fraction. Any of the minimum levels may be combined with a maximum level without limitation, save for the requirement that the minimum level be below the maximum water level. For example, in some embodiments, the extract may comprise ß-caryophyllene in an amount from 11% to 60% by weight of the total terpene fraction, for example, from 13% to 60%, from 14% to 60%, from 15% to 60%, from 15% to 50% or from 15% to 45% by weight of the terpene fraction.

The *Cannabis* extract may also comprise one or more of: ß-myrcene, D-limonene, linalool, a nerolidol (e.g. nerolidol 1 and/or 2) and a pinene (e.g. α-pinene and/or ß-pinene).

In some embodiments, the extract also comprises ß-myrcene. It is believed that ß-myrcene may enhance the bioavailability of the cannabinoids present in the extract and/or may assist in allowing the cannabinoids to pass the blood-brain-barrier. Myrcene may be present in the extract in an amount of at least 0.4% by weight of the total composition, for example, from 0.4% to about 40% by weight of the total composition. Myrcene may be present in the extract in an amount of up to 50% by weight of the terpene fraction, for example, from 0.05% to 50% by weight, from 0.05% to 25% by weight, from 0.05% to 5% by weight of the terpene fraction.

In some embodiments, the ratio of ß-caryophyllene to myrcene is greater than about 30:1, for example, 40:1, 50:1, 60:1, 70:1, 80:1, 90:1 or 97.5:1. In some embodiments, the ratio of ß-caryophyllene to myrcene is less than 170:1, for example, 160:1, 150:1, 140:1 or 130:1. In some embodiments, the ratio of ß-caryophyllene to myrcene is within a particular range of ratios, such as any combination of the above described ratios, for example, from 30:1 to 170:1, 40:1 to 160:1, 50:1 to 150:1, 60:1 to 140:1, 70:1 to 130:1, 80:1 to 120:1 or 90:1 to 110:1.

Limonene is a cyclic monoterpene having the molecular formula $C_{10}H_{16}$. There are a number of different naturally occurring isomers; however, the most common form is the dextrorotatory isomer, namely D-limonene. Limonene may be present in the extract in an amount of at least about 0.1% by weight of the terpene fraction, for example, from 0.1 to about 10% by weight of the terpene fraction. In some embodiments, limonene is absent from the extract, or only present in an amount below the limit of detection.

Linalool is a terpenoid that is found in many flower and spice plants having the molecular formula $C_{10}H_{18}O$. It is believed that when linalool is present in a *Cannabis* extract, that is may provide a sedative effect. In some embodiments, linalool may be present in an amount of at least 0.05% by weight of the terpene fraction. In some preferred embodiments, linalool is present in an amount of at least 5% by weight of the terpene fraction. In other embodiments, linalool is present in amount of from 0.05% to 25% by weight of the terpene fraction, for example, from 0.1% to 20% by weight of the terpene fraction.

Nerolidol is a sesquiterpenoid having the molecular formula of $C_{15}H_{26}O$. It exists in Nature in two isomeric forms, namely nerolidol 1 and nerolidol 2, which differ in the geometry around a central olefin, i.e. either cis or trans isomers. The extract may comprise nerolidol (i.e. both nerolidol 1 and nerolidol 2) in an amount of at least 0.01% by weight of the terpene fraction, for example, from 0.01% to 20% by weight of the terpene fraction. Typically, nerolidol 1 is present in greater amount relative to nerolidol 2; however, in other embodiments, nerolidol 2 may be present in a greater amount relative to nerolidol 1. The ratio of nerolidol 1 to nerolidol 2 may be about 1:1, about 2:1, about 2:1, about 3:1, about 1:3, about 4:1, about 1:4, about 5:1, or about 1:5. In some embodiments, nerolidol 1 or nerolidol 2 may be absent (or present in an amount below the limit of detection). Nerolidol 1 may be present in the extract in an amount of at least about 0.01% by weight of the terpene fraction, for example, from 0.01% to 20% or 0.1 to 15% by weight of the terpene fraction. Nerolidol 2 may be present in the extract in an amount of at least about 0.01% by weight of the terpene fraction, for example, 0.01% to 5% or 0.1% to 2% by weight of the terpene fraction.

Pinene is a bicyclic monoterpene having the molecular formula $C_{10}H_{16}$. Pinene is found in Nature in two isomeric forms: α-pinene and ß-pinene. The extract may comprise pinene (i.e. α-pinene and ß-pinene) in an amount of at least 5% by weight of the terpene fraction, for example, at least 6%, 8%, 10%, 15% or 20% by weight of the composition. In some embodiments, α-pinene is present in greater amount relative to ß-pinene. In other embodiments, ß-pinene is present in a greater amount relative to α-pinene. The ratio of α-pinene to ß-pinene may be about 1:1, about 2:1, about 2:1, about 10:1, about 1:10, about 15:1, about 1:15, about 20:1, about 1:20, about 25:1, about 1:25, about 30:1 or about 1:30. In some embodiments, α-pinene or ß-pinene may be absent (or present in an amount below the limit of detection). α-Pinene may be present in the extract in an amount of at least about 0.01% by weight of the terpene fraction, for example, from 0.01% to 5% by weight. ß-pinene may be present in the extract in an amount of at least about 0.01% by weight of the terpene fraction, for example, 0.01% to 50% or 5% to 40% by weight of the terpene fraction.

In some embodiments, the terpene fraction may be present in the composition in an amount from 0.01% to 6% by weight of the extract and may comprise:

ß-caryophyllene in an amount of from 11% to 50% by weight of the terpene fraction;

optionally ß-myrcene in an amount of from 0.01% to 40% by weight of the terpene fraction;

optionally D-limonene in an amount of from 0.01% to 10% by weight of the terpene fraction;

optionally linalool in an amount of from 5% to 20% by weight of the terpene fraction;

optionally ß-pinene in an amount of from 1% to 50% by weight of the terpene fraction;

optionally α-pinene in an amount of from 0.01% to 5% by weight of the terpene fraction;

optionally nerolidol 1 in an amount of from 0.01% to 20% by weight of the terpene fraction; and optionally nerolidol 2 in an amount of from 0.001% to 5% by weight of the terpene fraction.

In some embodiments, the extract further comprises humulene. It is believed that that humulene may enhance the sedative properties of the extract. Humulene is also sometimes called α-caryophyllene. Humulene may be present in the extract in an amount of at least about 1% by weight of the terpene fraction, for example, from about 1% to about 25% or about 5% to about 15% by weight of the terpene fraction.

In some embodiments, the ratio of humulene to myrcene is greater than about 12:1, for example, 14:1, 16:1, 18:1, 20:1, 22:1, 24:1, 25:1, 26:1, 27:1 or 28:1. In some embodiments, the ratio of humulene to myrcene is less than 50:1, for example, 45:1, 40:1, 38:1, 36:1, 34:1, 33:1, 32:1, 31:1 or 30:1. In some embodiments, the ratio of humulene to myrcene is within a particular range of ratios, such as any combination of the above described ratios, for example, from 14:1 to 50:1, 16:1 to 40:1, 18:1 to 38:1, 20:1 to 36:1, 22:1 to 34:1, 24:1 to 33:1 or 26:1 to 30:1.

The *Cannabis* extract may include additional terpenes and terpenoids which, it is believed, also potentiate the efficacy of the pharmaceutical compositions. These terpenes may include one or more of α-bisabolol, caryophyllene oxide, p-cymene, isopulegol, ocimene, α-terpinene, γ-terpinene, δ-s-carene, guaiol, and terpinolene.

In some embodiments, specific terpenes or terpenoids may be absent, or present in non-detectable amounts (e.g. less than 0.001% by weight of the analyte). In some embodiments, the *Cannabis* extract one or more of the following terpenes or terpenoids are absent, or present in non-detectable amounts: camphene, δ-s-carene, geraniol, guaiol and D-limonene.

One exemplary *Cannabis* extract is set out in the table below. Amounts of cannabinoids are reported as determined by high-performance liquid chromatography (HPLC) and amounts of terpenes are reported as determined by gas chromatography (GO). It will be appreciated that, as the *Cannabis* extract is derived from Nature, the amount of each component may vary in some cases by +/−10%, +/−25% or +/−50%. The ranges of amounts corresponding to each of these limits to account for the potential variation in the composition are also shown in the following table.

| Compound | Amount (wt % of total composition) | +/− 10% | +/− 25% | +/− 50% |
|---|---|---|---|---|
| THCA | 0.345 | 0.311-0.380 | 0.259-0.431 | 0.1725-0.5175 |
| THC | 55.131 | 49.618-60.644 | 41.348-68.914 | 27.5655-82.6965 |
| THCV | Not detected (ND) | | | |
| CBD | ND | | | |
| CBDA | ND | | | |
| CBG | 0.367 | 0.330-0.404 | 0.275-0.459 | 0.1835-0.5505 |
| CBN | ND | | | |
| CBC | ND | | | |
| α-bisabolol | 0.018 | 0.016-0.020 | 0.0135-0.0225 | 0.009-0.027 |
| camphene | ND | | | |
| δ-s-carene | ND | | | |
| ß-caryophyllene | 0.195 | 0.176-0.215 | 0.146-0.244 | 0.0975-0.2925 |
| caryophyllene oxide | 0.003 | 0.0027-0.0033 | 0.00225-0.00375 | 0.0015-0.0045 |
| p-cymene | 0.018 | 0.0162-0.0198 | 0.0135-0.0225 | 0.009-0.027 |
| geraniol | ND | | | |
| guaiol | ND | | | |
| α-humulene | 0.056 | 0.0504-0.0616 | 0.042-0.070 | 0.028-0.084 |
| isopulegol | 0.002 | 0.0018-0.0022 | 0.0015-0.0025 | 0.001-0.003 |
| D-limonene | ND | | | |
| linalool | 0.062 | 0.056-0.068 | 0.047-0.078 | 0.031-0.093 |
| ß-myrcene | 0.002 | 0.0018-0.0022 | 0.0015-0.0025 | 0.001-0.003 |
| nerolidol 1 | 0.036 | 0.032-0.040 | 0.027-0.045 | 0.018-0.054 |
| nerolidol 2 | 0.008 | 0.0072-0.0088 | 0.006-0.010 | 0.004-0.012 |
| ocimene | 0.005 | 0.0045-0.0055 | 0.00375-0.00625 | 0.0025-0.0075 |
| α-pinene | 0.001 | 0.0009-0.0011 | 0.00075-0.00125 | 0.0005-0.0015 |
| ß-pinene | 0.032 | 0.0288-0.0352 | 0.024-0.04 | 0.016-0.048 |
| α-terpinene | 0.001 | 0.0009-0.0011 | 0.00075-0.00125 | 0.0005-0.0015 |
| γ-terpinene | 0.001 | 0.0009-0.0011 | 0.00075-0.00125 | 0.0005-0.0015 |
| terpinolene | 0.002 | 0.0018-0.0022 | 0.0015-0.0025 | 0.001-0.003 |
| Mass (terpene fraction) | 0.442 | 0.3978-0.4862 | 0.3315-0.5525 | 0.221-0.663 |
| Mass (% of total extract) | 56.285 | 50.657-61.914 | 42.214-70.356 | 28.143-84.428 |

The pharmaceutical composition may further comprise one or more pharmaceutically acceptable carriers, diluents, adjuvants, excipients or any combination thereof.

The carrier, diluent, adjuvant and/or excipient are "pharmaceutically acceptable" meaning that they are compatible with the other ingredients of the composition and is not deleterious to a subject upon or following administration. The pharmaceutical compositions may be formulated, for example, by employing conventional solid or liquid vehicles or diluents, as well as pharmaceutical additives of a type appropriate to the mode of desired administration (for example, excipients, binders, preservatives, stabilisers, flavours, etc.) according to techniques such as those well known in the art of pharmaceutical formulation (See, for example, Remington: The Science and Practice of Pharmacy, 21st Ed., 2005, Lippincott Williams & Wilkins). The pharmaceutically acceptable carrier may be any carrier included in the United States Pharmacopeia/National Formulary (USP/NF), the British Pharmacopoeia (BP), the European Pharmacopoeia (EP), or the Japanese Pharmacopoeia (JP). In some embodiments, the carrier, diluent, adjuvant and/or excipient may be non-natural (e.g. synthetically produced).

The pharmaceutical composition includes those suitable for oral, rectal, nasal, topical (including buccal and sublingual), vaginal or parenteral (including intramuscular, subcutaneous and intravenous) administration or in a form suitable for administration by inhalation or insufflation.

The *Cannabis* extract, together with a conventional adjuvant, carrier, excipient or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For preparing pharmaceutical compositions from the *Cannabis* extract described herein, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

Liquid form preparations include solutions, dispersions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The *Cannabis* extract can be suspended in a pharmaceutically acceptable carrier, such as sterile water, sterile organic solvent or a mixture of both.

Other liquid form preparations include those prepared by combining the *Cannabis* extract with one or more naturally derived oils (e.g. an essential oil) or waxes. An "essential oil" is an oil derived by extraction (e.g. steam extraction, or contacting the plant material with an extractant) or pressing, which contains primarily hydrophobic, and generally fragrant, components of the plant material. Suitable naturally derived oils and waxes include Sesame oil, Olive oil, *Arnica* essential oil, Lavender essential oil, Lavender Spike essential oil, Frankincense essential oil, Lemongrass essential oil, Cinnamon Leaf essential oil, Rosemary Cineole essential oil, Rosemary essential oil, Bergamot essential oil, Myrrh essential oil, Sage essential oil, Coconut oil, Bees wax and Hemp oil.

The pharmaceutical compositions may be formulated for parenteral administration (e. g. by injection, for example bolus injection or continuous infusion) and may be presented in unit dose form in ampoules, pre-filled syringes, small volume infusion or in multi-dose containers optionally with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

The solvent or dispersion medium for the injectable solution or dispersion may contain any of the conventional solvent or carrier systems, and may contain, for example, water, ethanol, polyol (for example, glycerol, propylene glycol and liquid polyethylene glycol, and the like), suitable mixtures thereof, and vegetable oils.

Pharmaceutical forms suitable for injectable use may be delivered by any appropriate route including intravenous, intramuscular, intracerebral, intrathecal, epidural injection or infusion.

Sterile injectable solutions are prepared by incorporating the *Cannabis* extract in the required amount in the appropriate carrier with various other ingredients such as those enumerated above, as required, followed by sterilisation. Generally, dispersions are prepared by incorporating the various sterilised active ingredients into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile suspension of the active ingredient plus any additional desired ingredients.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active may be incorporated with excipients and used in the form of ingestible tablets, buccal tablets, troches, capsules, elixirs, suspensions, syrups, wafers, and the like.

The amount of active ingredient in therapeutically useful compositions should be sufficient that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations, including those that allow specific delivery of the active peptide to specific regions of the gut.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents.

Pharmaceutically acceptable carriers and/or diluents include any and all solvents, dispersion media, coatings, antibacterial and antifungal agents, isotonic and absorption delaying agents and the like.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the active ingredients may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension.

In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas.

The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier may form a gel in the nasal cavity. The powder composition may be presented in unit dose form for example in capsules or cartridges of, e.g. gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the dosage unit forms are dictated by and directly dependent on (a) the unique characteristics of the active material and the particular therapeutic effect to be achieved, and (b) the limitations inherent in the art of compounding such an active material for the treatment of cancer of an associated symptom in living subjects having a diseased condition in which bodily health is impaired.

Also described herein are compositions absent a carrier where the compositions are in unit dosage form. Accordingly, also provided is a medicament comprising the *Cannabis* extract.

In some embodiments, the pharmaceutical composition further comprises an active agent other than the *Cannabis* extract. Any suitable active agent may be used provided that the activity of the active agent and/or the *Cannabis* extract is not diminished when combined. Preferably, the active agent is an anti-cancer drug. Suitable anti-cancer drugs include trastuzumab (e.g., Herceptin®) or protein tyrosine kinase inhibitors (e.g. lapatinib (e.g., Tykerb®)). In some embodiments, the subject has previously been administered, or is currently being administered, an aromatase inhibitor. In some embodiments, the aromatase inhibitor is selected from aminoglutethimide, testolactone (e.g., Teslac®), anastrozole (e.g., Arimidex®), letrozole (e.g., Femara®), exemestane (e.g., Aromasin®), vorozole (e.g., Rivisor®), formestane (e.g., Lentaron®), megestrol acetate (e.g., Megase®), and fadrozole (e.g., Afema®). In some embodiments, a subject with breast cancer has previously been administered, or is currently being administered, an ER antagonist. In some embodiments, the subject has previously been determined to have ER positive breast cancer. Non-limiting exemplary ER antagonists include tamoxifen (e.g., Nolvadex®, Istubal®, and Valodex®) and fulvestrant (e.g., Faslodex®) or a combination thereof.

Methods of Treatment

In another aspect, also provided is a method for treating cancer or a symptom associated with cancer. The method comprising administering to a patient in need thereof an effective amount of the pharmaceutical composition described herein.

The pharmaceutical compositions may be used to treat cancer or a symptom associated with cancer. In particular, the pharmaceutical compositions may be effective in the treatment of a breast cancer, for example, HER2 positive, triple negative and/or hormone receptor positive breast cancer. In some embodiments, the breast cancer is HER2 positive breast cancer. HER2 positive breast cancer is one of the more aggressive forms of breast cancer, and accounts for about 20% of all breast cancers. HER2 is the abbreviation for "human epidermal growth factor receptor 2" which is a protein expressed by HER2 positive breast tumour cells. In some embodiments, the breast cancer is triple negative breast cancer. There are currently no targeted therapeutic options for triple negative breast cancer on the market. In some embodiments, the breast cancer is hormone receptor positive breast cancer. The inventors have shown that a Cannabis extract possesses efficacy against HER2+, triple negative and hormone receptor positive breast cancer cells. In addition, for THC-rich extracts (e.g. an extract comprising ≥0.3% w/w of the terpene fraction, ≥50% w/w $\Delta^9$-Tetrahydrocannabinol (THC); ≥0.3% w/w Cannabigerol (CBG); and ≤0.5% w/w Cannabinol (CBN), the inventors have shown that the Cannabis extract has greater activity against the tested breast cancer cells than THC alone (see FIGS. 5-8).

Figure 2:
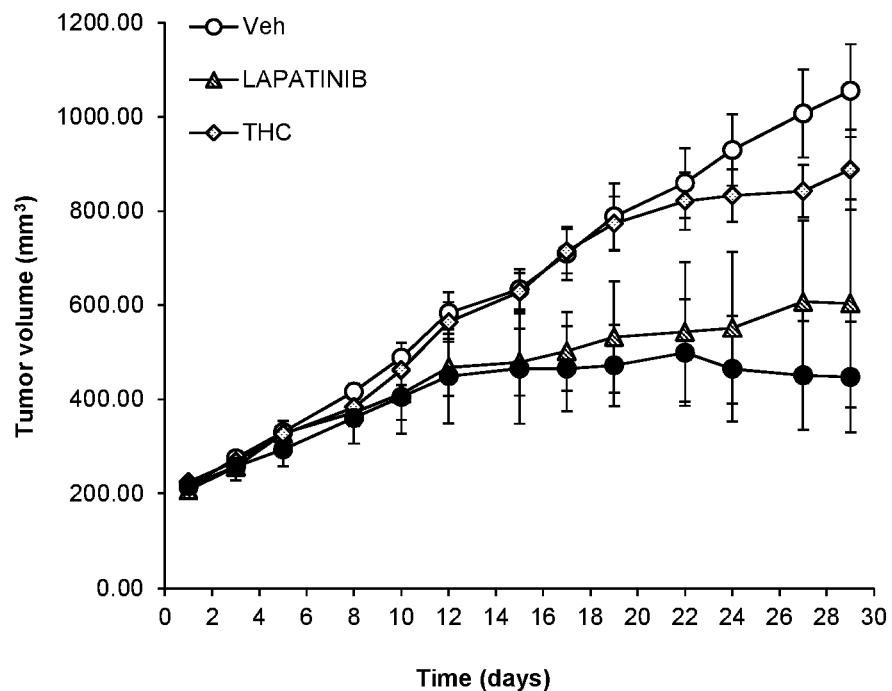
FIG. 2 shows a chart of tumour volume over time for ectopic xenografts of BT474 human breast HER2+ adenocarcinoma cells in female immunodeficient (nude) mice treated with (i) vehicle alone, (ii) lapatinib, (iii) THC, and (iv) the combination of lapatinib and THC.
Figure 3:
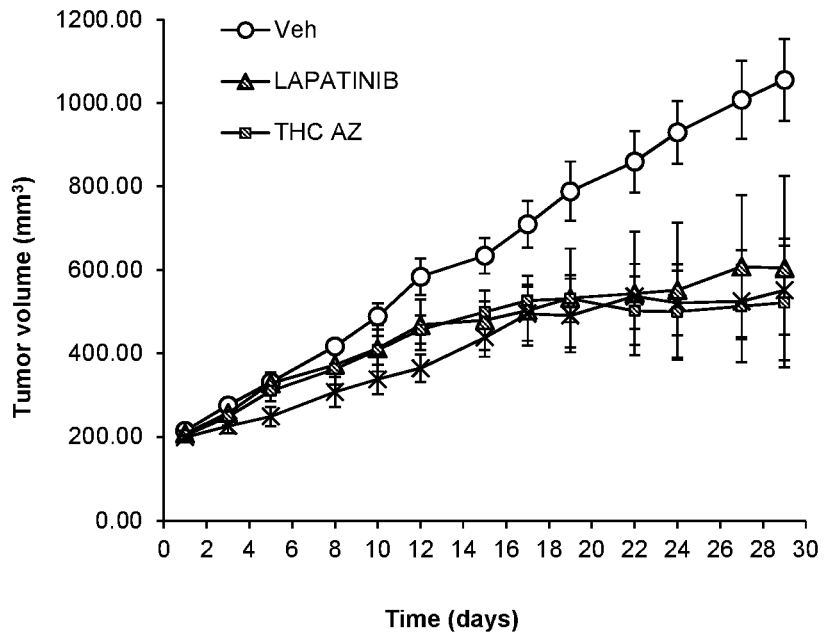
FIG. 3 shows a chart of tumour volume over time for ectopic xenografts of BT474 human breast HER2+ adenocarcinoma cells in female immunodeficient (nude) mice treated with (i) vehicle, (ii) lapatinib, (iii) a *Cannabis* extract, and (iv) the combination of lapatinib and the *Cannabis* extract.
Figure 4:
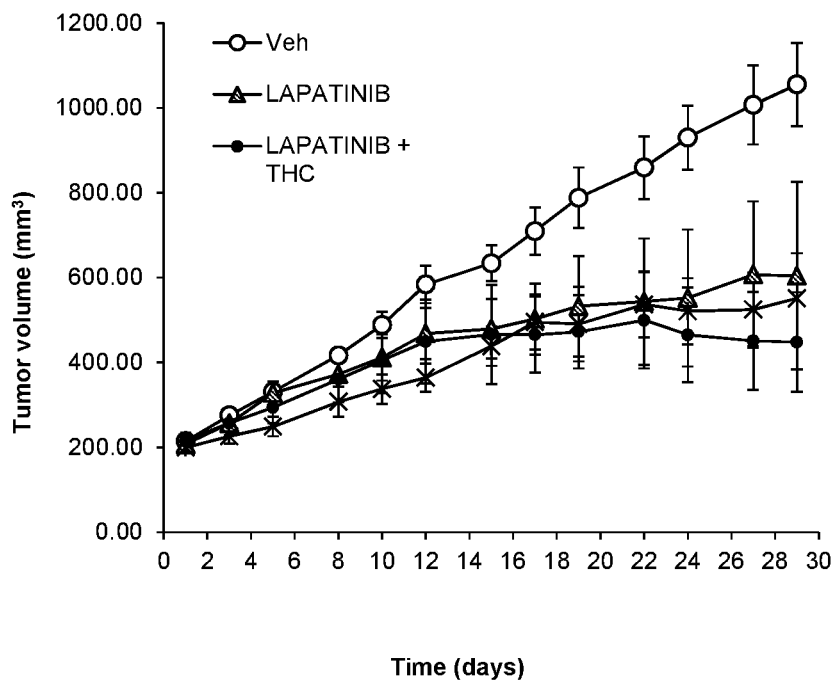
FIG. 4 shows a chart of tumor volume over time for ectopic xenografts of BT474 human breast HER2+ adenocarcinoma cells in female immunodeficient (nude) mice treated with (i) vehicle, (ii) lapatinib, (iii) the combination of lapatinib and THC.

The inventors observed that the volume of ectopic xenografts of human HER2 positive malignant cells are reduced following treatment with the pharmaceutical composition by similar volumes compared to the approved drug lapatinib (see FIGS. 1, 2 and 3). The reduction in tumour volume for the pharmaceutical compositions comprising a high-THC Cannabis extract are greater than those for an equivalent dose of THC alone.

Symptoms associated with cancer include unexplained weight loss, fever, fatigue, pain, and skin changes. Symptoms specifically associated with breast cancer include thickening or lumps forming in the breast tissue.

Symptoms of cancer are also commonly associated with many, if not all, of existing cancer therapies, including chemotherapy and radiotherapy. The present composition may also be used to treat the symptoms of cancer therapy.

By "effective amount" it is meant an amount sufficient that when administered to the patient an amount of the drug is provided to achieve an effect. In the case of a therapeutic method, this effect may be the treatment of cancer or a symptom associated with cancer. Therefore, the "effective amount" may be a "therapeutically effective amount". By "therapeutically effective amount" it is meant an amount sufficient that when administered to the patient an amount of drug is provided to treat the disease or a symptom of the disease.

As used herein, the terms "treating", "treatment", "treat" and the like mean affecting a subject, tissue or cell to obtain a desired pharmacological and/or physiological effect. The effect may be prophylactic in terms of completely or partially preventing, or reducing the severity of, a disease or associated symptom, and/or may be therapeutic in terms of a partial or complete cure of a disease. A reference to "treating" cancer therefore encompasses: (a) inhibiting cancer cell growth, e.g. arresting tumour development or further development; (b) relieving or ameliorating the effects of the cancer, i.e. causing regression of the effects of the cancer; (c) reducing the incidence of metastasis; or (d) preventing the cancer or symptom associated with cancer from occurring in a subject predisposed to cancer or at risk thereof so that the cancer does not develop or occur in the subject.

The method may comprise administering more than one pharmaceutical composition of the present invention to the patient in need thereof. For example, in some circumstances, it is preferred to administer a pharmaceutical composition high in THC and a pharmaceutical composition high in CBD to the patient. These compositions may be administered in an alternating order and separated by a period of time. The pharmaceutical composition high in THC may comprise ≥50% w/w THC, ≥0.3% w/w CBG, ≤0.5% w/w CBN and ≥0.3% w/w terpene fraction. The pharmaceutical composition high in CBD may comprise ≥60% w/w CBD, ≤3% w/w THC, ≤0.1% w/w CBN and ≥0.5% w/w terpene fraction.

The method may also comprise administering an active agent other than the Cannabis extract. This active agent may be administered simultaneously or consecutively with the Cannabis extract. By consecutively it is meant that each of the Cannabis extract and the other active agent are administered separately and may be at different times. Typically, when the Cannabis extract and the other active agent are administered consecutively they are administered within 24 hours, or within 12, 8, 6, 5, 4, 3, 2, or 1 hour(s) of each other. The Cannabis extract may be administered before or after the other active agent. Further, the route of administration for the Cannabis extract and the other active agent may be the same or different.

In another aspect, also provided is the use of the Cannabis extract in the preparation of a medicament for the treatment of cancer or a symptom associated with cancer.

Also provided is a kit comprising in separate parts:
(a) an effective amount of the Cannabis extract; and
(b) a pharmaceutically acceptable carrier, diluent, adjuvant, excipient or a combination thereof.

In some embodiments, the kit may comprise in a separate part (b') an effective amount of an active agent other than the Cannabis extract. Part (b') may be included in the kit, in addition to parts (a) and (b), or in place of part (b).

In another aspect, there is provided the pharmaceutical composition for treating cancer or a symptom associated with cancer. The pharmaceutical composition may be any of the pharmaceutical compositions described above, comprising any above-described combination of components, provided that it comprises the Cannabis extract with the specified terpene fraction. The cancer and its symptoms may also be any of those described above.

EXAMPLES

The invention will be further described by way of non-limiting examples. It will be understood to persons skilled in the art of the invention that many modifications may be made without departing from the spirit and scope of the invention.

Example 1—THC Compositions

The following THC compositions are described:
AZ1—extract of Purple UrkI Cannabis plant.
AZ2—extract of Granddaddy Purple Cannabis plant.
AZ3—extract of Sensi Star Cannabis plant.
AZ4—extract of Ogre Kush Cannabis plant.
AZ5—extract of Harletsu Cannabis plant.
AZ6—extract of ACDC Cannabis plant.

| | Component | | | | | |
|---|---|---|---|---|---|---|
| | AZ1 wt %[3] | AZ2 wt %[3] | AZ3 wt %[3] | AZ4 wt %[3] | AZ5 wt %[3] | AZ6 wt %[3] |
| Cannabinoids[1] | | | | | | |
| THCA | 0.345 | 0.497 | 2.918 | 0.002 | 1.161 | 0.275 |
| THC | 55.131 | 75.442 | 65.066 | 75.127 | 2.876 | 2.717 |
| THCV | 0.000 | 0.899 | 0.436 | 0.265 | 0 | 0 |
| CBD | 0.000 | 0.000 | 0.000 | 0.000 | 65.304 | 61.298 |
| CBDA | 0.000 | 0.000 | 0.000 | 0.000 | 0 | 0.239 |
| CBG | 0.367 | 2.047 | 2.525 | 1.453 | 1.563 | 1.187 |
| CBGA | — | 0.000 | 1.252 | — | 0.176 | 0 |
| CBN | 0.000 | 0.637 | 0.433 | 0.052 | 0 | 0 |
| CBC | 0.000 | 0.995 | 0.747 | 1.092 | 3.303 | 0.123 |
| Terpenes[2] | | | | | | |
| α-bisabolol | 0.018 | 0.016 | 0.007 | 0.013 | 0.006 | 0.016 |
| camphene | 0.000 | 0.000 | 0.000 | 0.000 | 0.000 | 0 |
| δ-s-carene | 0.000 | 0.004 | 0.001 | 0.000 | 0.010 | 0.005 |
| β-caryophyllene | 0.195 | 0.220 | 0.053 | 0.226 | 0.080 | 0.195 |
| caryophyllene oxide | 0.003 | 0.004 | 0.002 | 0.002 | 0.003 | 0.004 |
| p-cymene | 0.018 | 0.000 | 0.000 | 0.071 | 0.003 | 0.004 |
| geraniol | 0.000 | 0.000 | 0.000 | 0.000 | 0.000 | 0 |
| guaiol | 0.000 | 0.026 | 0.009 | 0.006 | 0.008 | 0.037 |
| α-humulene | 0.056 | 0.072 | 0.023 | 0.044 | 0.029 | 0.062 |
| isopulegol | 0.002 | 0.007 | 0.004 | 0.000 | 0.005 | 0.008 |
| D-limonene | 0.000 | 0.025 | 0.015 | 0.000 | 0.033 | 0.035 |
| linalool | 0.062 | 0.113 | 0.026 | 0.070 | 0.001 | 0.056 |
| β-myrcene | 0.002 | 0.007 | 0.003 | 0.007 | 0.009 | 0.009 |
| nerolidol 1 | 0.036 | 0.071 | 0.020 | 0.001 | 0.015 | 0.011 |
| nerolidol 2 | 0.008 | 0.009 | 0.005 | 0.000 | 0.004 | 0.007 |
| ocimene | 0.005 | 0.012 | 0.032 | 0.030 | 0.027 | 0.009 |
| α-pinene | 0.001 | 0.004 | 0.000 | 0.003 | 0.004 | 0.005 |
| β-pinene | 0.032 | 0.066 | 0.093 | 0.283 | 0.132 | 0.125 |
| α-terpinene | 0.001 | 0.003 | 0.000 | 0.001 | 0.011 | 0.005 |
| γ-terpinene | 0.001 | 0.003 | 0.001 | 0.000 | 0.006 | 0.004 |
| terpinolene | 0.002 | 0.006 | 0.006 | 0.025 | 0.144 | 0.006 |
| total terpenes | 0.442 | 0.666 | 0.300 | 0.783 | 0.531 | 0.601 |
| total | 56.285 | 81.185 | 73.677 | 78.773 | 74.913 | 66.442 |

Notes:
[1] Cannabinoids were detected using HPLC analysis, an amount reported as 0 wt % indicates that the compound was either not detected, or present in an amount below the detection limit of the HPLC;
[2] Terpenes were detected using GC analysis, an amount reported as 0 wt % indicates that the compound was either not detected, or present in an amount below the detection limit of the GC;
[3] In order to allow for Natural variation, amount within +/− 10%, +/− 25% or +/− 50% of the reported values.

Example 2—In Vivo Study Comparing Compositions Comprising a *Cannabis* Extract, THC Only and Lapatinib Against HER2 Positive Tumour Volume Methodology. 5×10[6] viable BT474 human breast HER2+ adenocarcinoma cells were subcutaneously injected into the right flank of 6-week-old athymic mice. When tumors reached circa 200 mm[3], animals were randomly assigned to the following experimental groups and the indicated treatments were started and maintained for 4 weeks:

VEHICLE: sesame oil (THC vehicle, 3 times/week)+ 0.5% hydroxypropylmethyl cellulose+0.1% Tween 80, in water (Lapatinib vehicle, daily)

LAPATINIB (100 mg/Kg, daily)
THC (45 mg/Kg, 3 times/week)
THC+LAPATINIB
THC AZ (45 mg/Kg THC, 3 times/week). THC AZ comprises vehicle (sesame oil) and AZ1 as described in Example 1.
THC AZ+LAPATINIB All treatments were administered by oral gavage. Tumors were routinely measured with external caliper, and volume was calculated as $(4\pi/3) \times (width/2)^2 \times (length/2)$.

Results are shown in FIGS. 1-4. In can be seen from FIG. 1 that treatment with the THC AZ composition results in a greater reduction in tumor volume than treatment with the THC only and vehicle only treatments. Further, the efficacy of THC AZ is approximately the same as the approved chemotherapy lapatinib (see FIGS. 2-4). Further, these data suggest that the combination therapy of THC AZ and lapatinib is non-deleterious (FIG. 3).

Example 3—In Vitro Study of Efficacy of Pure THC and *Cannabis* Extract (THC-Rich Extract) Against Various Breast Cancer Cells Cancer cells were plated at a density of 5000 cells/cm[2] and incubated in the media indicated below for 24 h at 37° C. and 5% $CO_2$ atmosphere:

| | CELL LINE | CULTURE MEDIUM | SUPPLEMENTS |
|---|---|---|---|
| ER+/PR+ | MCF7 | MEM | 10% FBS |
| | | | 50 U/mL P/S |
| | | | 2 mM L-Glutamine |
| | | | 10 μg/mL Insuline |
| | T47D | RPMI | 10% FBS |
| | | | 50 U/mL P/S |
| | | | 10 μg/mL Insuline |
| HER2+ | HCC 1954 | RPMI | 10% FBS |
| | | | 50 U/mL P/S |
| | SKBR3 | McCoy's 5A | 10% FBS |
| | | | 50 U/mL P/S |
| | | | 1% Glutamine |
| Triple negative | MDA-MD-231 | DMEM | 10% FBS |
| | | | 50 U/mL P/S |
| | SUM 159 | Ham's F12 | 5% FBS |
| | | | 50 U/mL P/S |
| | | | 5 μg/mL Insuline |
| | | | 0.5 μg/mL HC |

FBS: fetal bovine serum;
P/S: penicillin/streptomycin;
HC: hydrocortisone

Cells were then transferred to serum-free medium for 5 h and after that, challenged with the corresponding treatments (pure THC, THC-rich extract (AZ1) or the corresponding vehicle -DMSO-). Cell viability was determined after 24 h incubation with the different treatments by violet crystal staining: 0.1% violet crystal in 20% methanol was added to the wells, and after a 20 min incubation at room temperature, the stained cells were resuspended in methanol. Cell viability was determined by measuring absorbance at 570 nm, and expressed as % versus vehicle-treated cells (set at 100%).

Figure 5:
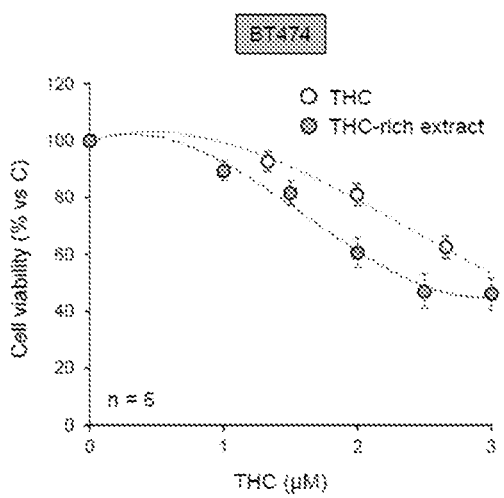
FIG. 5 shows a series of charts comparing the activity of THC and a *Cannabis* extract (THC-rich extract) against (A) BT474 cells, (B) HCC1954 cells and (C) SKBR3 cells. BT474, HCC1954 and SKBR3 cells are all HER2+ breast cancer cells.
Figure 5:
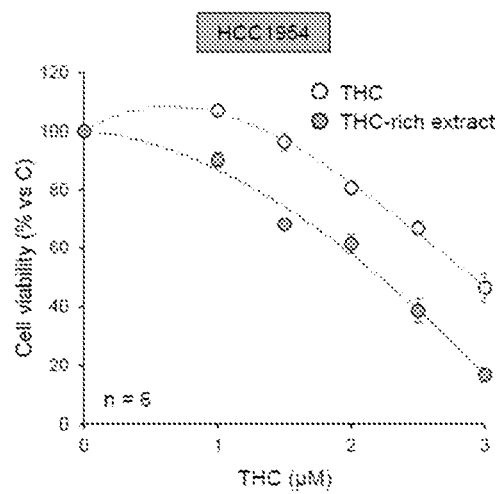
Figure 5:
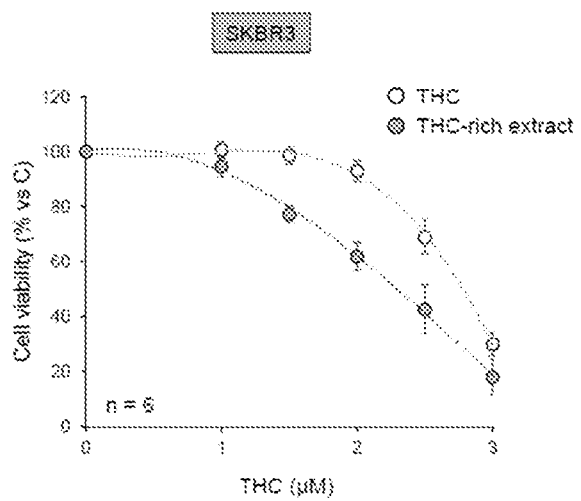
Figure 6:
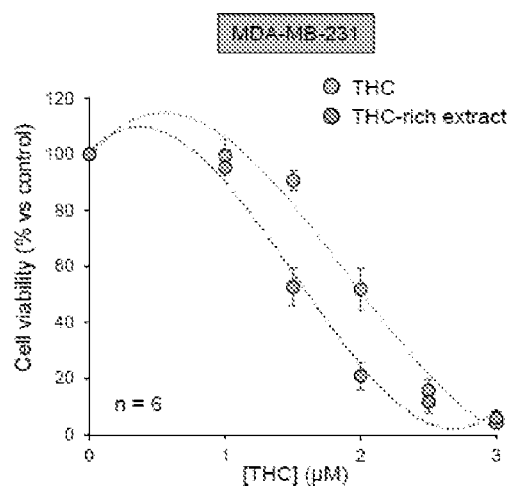
FIG. 6 shows a series of charts comparing the activity of THC and a *Cannabis* extract against (A) MDA-MB-231 cells and (B) SUM159 cells. MDA-MB-231 and SUM159 cells are triple negative breast cancer cells.
Figure 6:
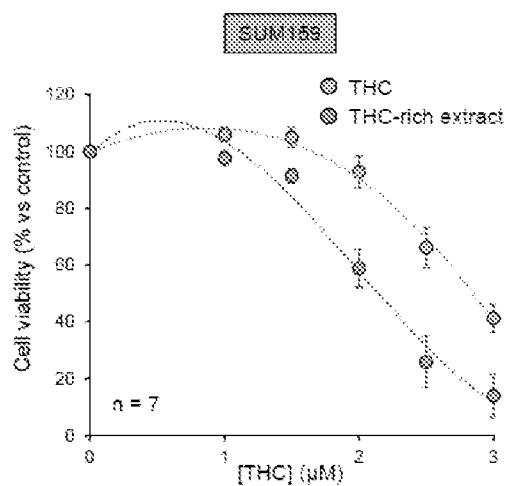
Figure 7:
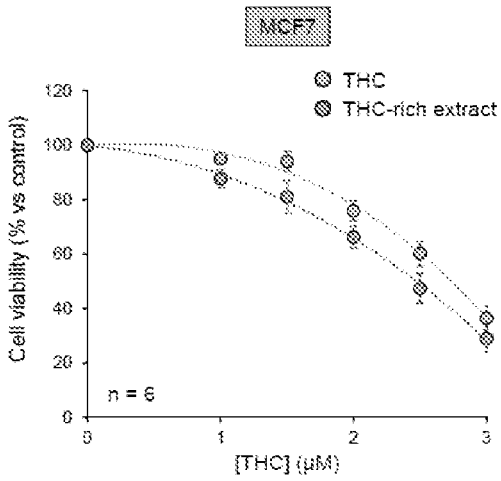
FIG. 7 shows a series of charts comparing the activity of THC and a *Cannabis* extract against (A) MCF7 cells and (B) T47D cells. MCF7 and T47D cells are hormone receptor positive breast cancer cells.
Figure 7:
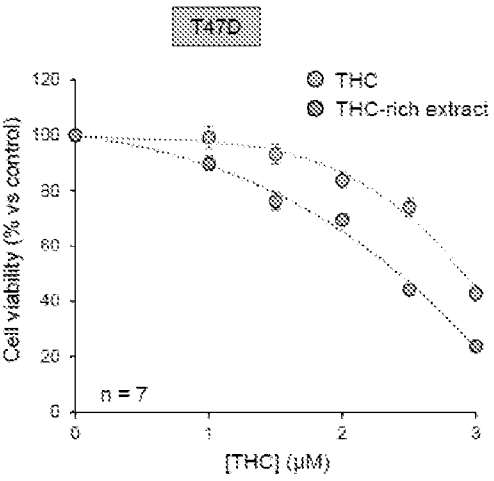

The results of these experiments are shown in FIGS. 5-7. In each experiment, the *Cannabis* extract demonstrated enhanced efficacy relative to THC alone. The *Cannabis* extract demonstrated enhanced efficacy relative to THC alone against each of the tested HER2 positive (FIG. 5), triple negative (FIG. 6) and hormone receptor positive (FIG. 7) breast cancer cells.

Figure 8:
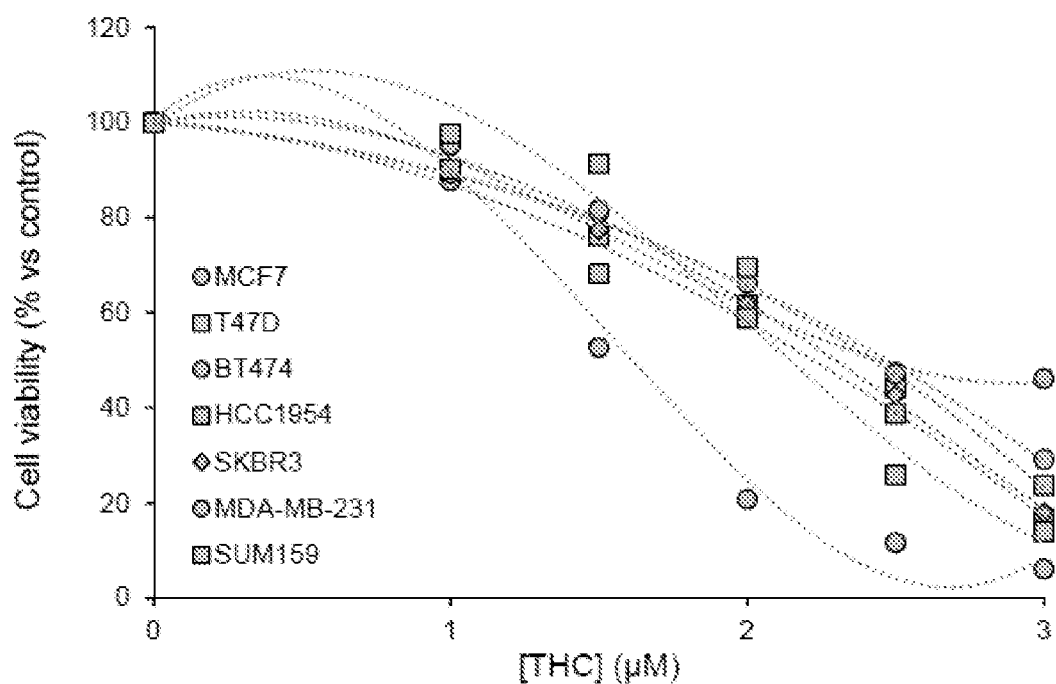
FIG. 8 shows a chart of cell viability as a percentage versus control of the various breast cancer cells after treatment with a *Cannabis* extract.

The results of this example are summarised in FIG. 8, which shows that the *Cannabis* extract is effective against all cancer cell lines tested.

Unless the context requires otherwise, all percentages referred to herein are percentages by weight of the pharmaceutical composition.

The term "about", when used to describe a value, preferably means an amount within ±10% of that value.

The terms "a", "an", "and" and/or "the" and similar referents in the context of describing the invention and the claims which follow are to be construed to cover both the singular and the plural, unless otherwise indicated herein or clearly contradicted by context.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A pharmaceutical composition comprising a *Cannabis* extract and optionally one or more pharmaceutically acceptable carriers, diluents, adjuvants, excipients or any combination thereof, the *Cannabis* extract comprising a cannabinoid fraction and a terpene fraction, wherein the *Cannabis* extract comprises:

A:
≥0.3% w/w of the terpene fraction;
≥50% w/w $\Delta^9$-Tetrahydrocannabinol (THC);
≥0.3% w/w Cannabigerol (CBG); and
≤0.5% w/w Cannabinol (CBN);

wherein the terpene fraction comprises:
ß-caryophyllene in an amount of at least 11% by weight of the terpene fraction,
linalool in an amount of at least 5% by weight of the terpene fraction; and
ß-pinene in an amount of at least 1% by weight of the terpene fraction.

2. The pharmaceutical composition of claim 1, wherein the *Cannabis* extract is a *Cannabis* oil.

3. The pharmaceutical composition of claim 1, wherein, for composition A, the *Cannabis* extract comprises $\Delta^9$-tetrahydrocannabinol (THC) in an amount of from 50% to 99% by weight of the pharmaceutical composition.

4. The pharmaceutical composition of claim 1, wherein the *Cannabis* extract comprises one or more additional cannabinoids selected from $\Delta^9$-Tetrahydrocannabinolic acid (THCA), $\Delta^9$-Tetrahydrocannabivarin (THCV), and (−)-Cannabidivarin (CBDV).

5. The pharmaceutical composition of claim 1, wherein the terpene fraction further comprises one or more of ß-myrcene, D-limonene, a nerolidol and α-pinene.

6. The pharmaceutical composition of claim 1, wherein the terpene fraction further comprises one or more of α-bisabolol, caryophyllene oxide, p-cymene, isopulegol, ocimene, α-terpinene, γ-terpinene, δ-s-carene, guaiol, and terpinolene.

7. The pharmaceutical composition of claim 1, wherein the pharmaceutically acceptable carrier is sesame oil.

8. The pharmaceutical composition of claim 1, further comprising an active agent other than the *Cannabis* extract.

9. The pharmaceutical composition of claim 1 for treating cancer or a symptom associated with cancer.

* * * * *